(12) United States Patent
Mafi et al.

(10) Patent No.: US 8,206,430 B2
(45) Date of Patent: Jun. 26, 2012

(54) ENDOLUMENAL SEALANT DELIVERY APPARATUS AND METHODS

(75) Inventors: Masoumeh Mafi, Santa Rosa, CA (US); Walter Bruszewski, Guerneville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 796 days.

(21) Appl. No.: 12/106,421

(22) Filed: Apr. 21, 2008

(65) Prior Publication Data
US 2009/0264821 A1    Oct. 22, 2009

(51) Int. Cl.
*A61F 2/06* (2006.01)
(52) U.S. Cl. ...................................................... 623/1.11
(58) Field of Classification Search .................. 623/1.11; 606/191; 604/96.01–103.14
See application file for complete search history.

(56) References Cited

U.S. PATENT DOCUMENTS

| | | | | |
|---|---|---|---|---|
| 4,364,392 A * | 12/1982 | Strother et al. | ............... | 606/195 |
| 4,994,033 A * | 2/1991 | Shockey et al. | .......... | 604/101.02 |
| 5,049,132 A * | 9/1991 | Shaffer et al. | ............ | 604/101.02 |
| 5,213,576 A * | 5/1993 | Abiuso et al. | ............ | 604/103.01 |
| 5,304,135 A * | 4/1994 | Shonk | ...................... | 604/103.11 |
| 5,318,531 A * | 6/1994 | Leone | ...................... | 604/103.01 |
| 5,342,305 A * | 8/1994 | Shonk | ...................... | 604/101.02 |
| 5,366,442 A * | 11/1994 | Wang et al. | .................... | 604/103 |
| 5,405,472 A * | 4/1995 | Leone | ........................... | 156/218 |
| 5,447,497 A * | 9/1995 | Sogard et al. | ........... | 604/101.02 |
| 5,512,051 A * | 4/1996 | Wang et al. | ............. | 604/103.14 |
| 5,514,092 A * | 5/1996 | Forman et al. | ........... | 604/101.03 |
| 5,540,798 A * | 7/1996 | DeMaio et al. | ............... | 156/200 |
| 5,611,775 A * | 3/1997 | Machold et al. | .............. | 604/509 |
| 5,662,712 A * | 9/1997 | Pathak et al. | .............. | 623/23.64 |
| 5,665,063 A * | 9/1997 | Roth et al. | ..................... | 604/509 |
| 5,709,653 A * | 1/1998 | Leone | .............................. | 604/20 |
| 5,833,682 A * | 11/1998 | Amplatz et al. | ................. | 606/15 |
| 6,537,195 B2 * | 3/2003 | Forman | ............................. | 600/3 |
| 6,544,223 B1 * | 4/2003 | Kokish | ..................... | 604/103.01 |
| 6,585,926 B1 * | 7/2003 | Mirzaee | ........................ | 264/400 |
| 7,041,046 B2 * | 5/2006 | Forman | ............................. | 600/3 |
| 7,115,299 B2 * | 10/2006 | Kokish | .......................... | 427/2.24 |
| 7,264,632 B2 | 9/2007 | Wright et al. | | |
| 7,658,966 B2 * | 2/2010 | Kokish | ........................... | 427/2.1 |
| 7,670,364 B2 * | 3/2010 | Dusbabek et al. | ........... | 623/1.11 |
| 2005/0171598 A1 | 8/2005 | Schaeffer | | |
| 2006/0292206 A1 * | 12/2006 | Kim et al. | ..................... | 424/443 |
| 2008/0003542 A1 * | 1/2008 | Jin et al. | ......................... | 433/224 |
| 2008/0255511 A1 * | 10/2008 | Krivoruchko | ............ | 604/103.08 |
| 2010/0189876 A1 * | 7/2010 | Kokish et al. | ................... | 427/2.3 |

* cited by examiner

*Primary Examiner* — Melanie Tyson
*Assistant Examiner* — Son Dang

(57) ABSTRACT

Endolumenally sealing a zone around the puncture and dilation area of a stent-graft fenestration or sealing the juncture between two lumens with an expandable sealant delivery device. In exemplary embodiments, an expandable sealant delivery device includes a catheter mounted balloon, which has a microporous membrane or a plurality of pores suitable for delivering a surgical sealant.

22 Claims, 13 Drawing Sheets

ENDOLUMENAL SEALANT DELIVERY APPARATUS AND METHODS

FIELD OF THE INVENTION

The invention relates to sealant delivery apparatus and methods for delivering sealants at stent-graft implantation sites.

BACKGROUND OF THE INVENTION

Tubular prostheses such as stents, grafts, and stent-grafts (e.g., stents having an inner and/or outer covering comprising graft material and which may be referred to as covered stents) have been used to treat abnormalities in passageways in the human body. In vascular applications, these devices often are used to replace or bypass occluded, diseased or damaged blood vessels such as stenotic or aneurysmal vessels. For example, it is well known to use stent-grafts, which comprise biocompatible graft material (e.g., Dacron® or expanded polytetrafluoroethylene (ePTFE) or some other polymer) supported by a framework (e.g., one or more stent or stent-like structures), to treat or isolate aneurysms. The framework provides mechanical support and the graft material or liner provides a blood barrier.

Aneurysms generally involve abnormal widening of a duct or canal such as a blood vessel and generally appear in the form of a sac formed by the abnormal dilation of the duct or vessel wall. The abnormally dilated wall typically is weakened and susceptible to rupture. Aneurysms can occur in blood vessels such as in the abdominal aorta where the aneurysm generally extends below the renal arteries distally to or toward the iliac arteries.

In treating an aneurysm with a stent-graft, the stent-graft typically is placed so that one end of the stent-graft is situated proximally or upstream of the diseased portion of the vessel and the other end of the stent-graft is situated distally or downstream of the diseased portion of the vessel. In this manner, the stent-graft extends through the aneurysmal sac and beyond the proximal and distal ends thereof to replace or bypass the weakened portion. The graft material typically forms a blood impervious lumen to facilitate endovascular exclusion of the aneurysm.

Such prostheses can be implanted in an open surgical procedure or with a minimally invasive endovascular approach. Minimally invasive endovascular stent-graft use is preferred by many physicians over traditional open surgery techniques where the diseased vessel is surgically opened, and a graft is sutured into position bypassing the aneurysm. The endovascular approach, which has been used to deliver stents, grafts, and stent-grafts, generally involves cutting through the skin to access the lumen of a vessel of the vasculature. Alternatively, lumenar or vascular access may be achieved percutaneously via successive dilations at a less traumatic entry point. Once access is achieved, the stent-graft can be routed through the vasculature to the target site. For example, a stent-graft delivery catheter loaded with a stent-graft can be percutaneously introduced into the vasculature (e.g., into a femoral artery) and the stent-graft delivered endovascularly to a position where it spans the aneurysm where it is to be deployed.

When using a balloon expandable stent-graft, balloon catheters generally are used to expand the stent-graft after it is positioned at the target site. When, however, a self-expanding stent-graft is used, the stent-graft generally is radially compressed or folded and held compressed at the distal end of a sheath or delivery catheter and self expands upon retraction or removal of the sheath at the target site. More specifically, a delivery catheter having coaxial inner and outer tubes arranged for relative axial movement therebetween can be used and loaded with a compressed self-expanding stent-graft. The stent-graft is positioned within the distal end of the outer tube (sheath) and in front of a stop fixed to the inner tube near its distal. Once the catheter is positioned for deployment of the stent-graft at the target site, the inner tube is held stationary and the outer tube (sheath) withdrawn so that the stent-graft is gradually exposed and expands. The inner tube or plunger prevents the stent-graft from moving back as the outer tube or sheath is withdrawn. An exemplary stent-graft delivery system is described in U.S. Pat. No. 7,264,632 to Wright et al and is entitled Controlled Deployment Delivery System, the disclosure of which is hereby incorporated herein in its entirety by reference.

Regarding proximal and distal positions referenced herein, the proximal end of a prosthesis (e.g., stent-graft) is the end closest to the heart (by way of blood flow) whereas the distal end is the end furthest away from the heart during deployment. In contrast, the distal end of a catheter (delivery system) is usually identified as the end that is farthest from the operator, while the proximal end of the catheter is the end nearest the operator.

Although the endovascular approach is much less invasive, and usually requires less recovery time and involves less risk of complication as compared to open surgery, there can be challenges with relatively complex applications such as those involving branch vessels. Branch vessel techniques have involved the delivery of a main device (e.g., a graft or stent-graft) and then a secondary device (e.g., a branch graft or branch stent-graft) through a fenestration or side opening in the main device and into a branch vessel. One example is when an aortic abdominal aneurysm is to be treated and its proximal neck is diseased or damaged to reduce the landing zone for the proximal end of the stent graft to the extent that it cannot support a connection and/or seal with a prosthesis. In this case, grafts or stent-grafts have been provided with fenestrations or openings formed in their side wall below a proximal portion (end) thereof to perfuse the branch vessels. The proximal portion is secured to the aortic wall above the renal arteries and the fenestrations or openings are aligned with the renal arteries. However, preformed openings may not properly align with target branch vessels.

Fenestration in situ has been an alternative approach to the perfuse a branch vessel of the abdominal aorta in an abdominal aortic aneurysm (AAA) stent-graft placement procedure and thoracic aorta in a thoracic aortic aneurysm (TAA) stent-graft placement procedure where the branch vessels are initially covered because stent-graft fixation can only be made proximal to these vessels. However, puncture and dilation of the stent-graft to form the fenestration at the location of the branch vessels results in tears in currently available woven graft cloth. The tears can propagate further over time, and can perhaps result in poor sealing between a branch vessel stent-graft positioned in the fenestration and the main stent-graft.

There remains a need to develop and/or improve methods for in situ stent-graft fenestration techniques.

SUMMARY OF THE INVENTION

An endolumenal sealant delivery apparatus for delivering sealant in a vessel of a human body comprises a catheter; an expandable balloon having a region having a plurality of micropores adapted to allow surgical sealant to pass therethrough; said balloon being coupled to the catheter. Among the many advantages of this embodiment is that it can deliver sealant to the perimeter of a stent-graft fenestration to prevent or minimize the risk of fenestration tear propagation. Another advantage is that the adhesive may enhance the seal between the branch vessel stent-graft and the graft material surrounding the fenestration in the fenestrated stent-graft.

A method of delivering sealant in a patient comprises endovascularly delivering a device into a graft fenestration in a human patient; and expanding the device and delivering surgical sealant therefrom to the graft material surrounding the fenestration.

Another method of sealing two overlapping graft members together comprises positioning a balloon, which has sealant delivery pores, in the region where the graft members overlap with the sealant delivery pores aligned with the region; inflating the balloon; and passing sealant through the pores and into the region where the graft members overlap.

A surgical sealant comprises radiopaque contrast medium dispersed in the sealant in a sufficient amount to enable fluoroscopic visualization of the sealant when delivered in a human patient.

In addition to the brief description contained herein, other features, advantages, and embodiments according to the present invention will be apparent to those skilled in the art from the following description and accompanying drawings, wherein, for purposes of illustration only, specific embodiments are set forth in detail.

BRIEF DESCRIPTION OF THE DRAWINGS

FIG. 4A depicts delivery of the sealant delivery balloon in an uninflated state to the stent-graft cover opening after the angioplasty balloon catheter has been withdrawn; FIG. 4B illustrates the sealant delivery balloon of FIG. 4A in an expanded state and delivering sealant after which the sealant delivery balloon is deflated and withdrawn into the guide catheter used to deliver the sealant delivery balloon and the sealant delivery balloon and guide catheter are removed while leaving the guidewire in place; FIG. 4C illustrates a branch vessel stent-graft in the process of being delivered to the stent-graft cover opening; and FIG. 4D illustrates the branch vessel stent-graft of FIG. 4C expanded in the opening, extending into the to the branch vessel.

FIG. 5A depicts positioning a puncture catheter to puncture the stent-graft, FIG. 5B illustrates delivering the sealant delivery apparatus of FIG. 1A in the opening formed by the puncture catheter, FIG. 5C illustrates delivering sealant from the sealant delivery apparatus after the apparatus has been inflated; FIG. 5D illustrates removal of the sealant delivery apparatus, and FIG. 5E illustrates delivery of a branch vessel stent-graft to the site.

DETAILED DESCRIPTION

The following description will be made with reference to the drawings where when referring to the various figures, it should be understood that like numerals or characters indicate like elements. Further, when referring to catheters, delivery devices, and loaded fasteners described below, the proximal end is the end nearest the operator and the distal end is farthest from the operator. While when referring to stent grafts delivered, their proximal end is the one nearest by way of blood flow path from the heart, while the distal end is the end farthest from the heart by way of blood flow path.

One embodiment generally involves endolumenally sealing a zone around the puncture and dilation area of a stent-graft fenestration with an expandable sealant delivery device. The sealant can be any suitable surgical sealant such as any sealant selected from the group consisting of surgical cyanoacrylate, fibrin sealants, collagen, and polyehthylene glycol polymers or bioglues, CoSeal®, Floseal®, or Onyx® adhesive, which is a biocompatible polymer (ethylene-vinyl alcoholcopolymer EVOH) dissolved in its organic solvent, dimethylsulfoxide (DMSO), where the sealant is modified for slow cure. Such slow cure sealants are commercially available.

According to one embodiment, the expandable sealant delivery device can be a balloon, which is mounted on a catheter and which has a microporous membrane suitable for delivering the desired sealant. In this embodiment, the device can perform in situ dilatation of a previously formed fenestration, while weeping or delivering surgical sealant to the fenestration zone. One of the many advantages of this arrangement is that it can prevent or minimize the risk of tears, which were created during the graft puncture and dilation steps performed to created the fenestration, from propagating in the graft material. Another advantage is that the adhesive enhances the seal between the branch vessel stent-graft and the graft material surrounding the fenestration in the fenestrated stent-graft.

According to another embodiment, a radiopaque contrast medium is dispersed in any one of the sealants described above in a sufficient amount to enable fluoroscopic visualization of the sealant when delivered in a human patient. This provides one mechanism to assist the physician in locating the position of sealant delivery in situ. For example, fine particles of tungsten, metallic silver, gold, iridium, platinum, or an alloy of any of these materials can be added to any of the sealants in an amount sufficient to be visually detected using conventional fluoroscopic techniques.

Figure 1A:
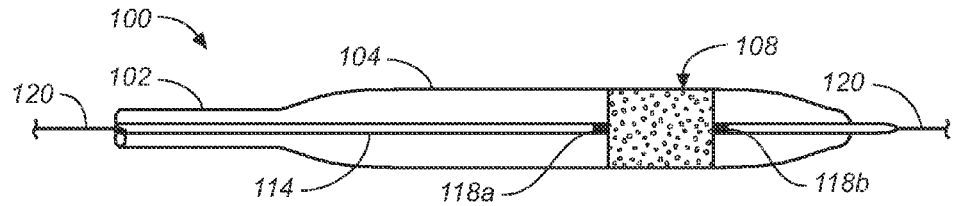
FIG. 1A illustrates one embodiment of expandable sealant delivery apparatus according to the invention where the apparatus is shown in a partially expanded state.
Figure 1B:
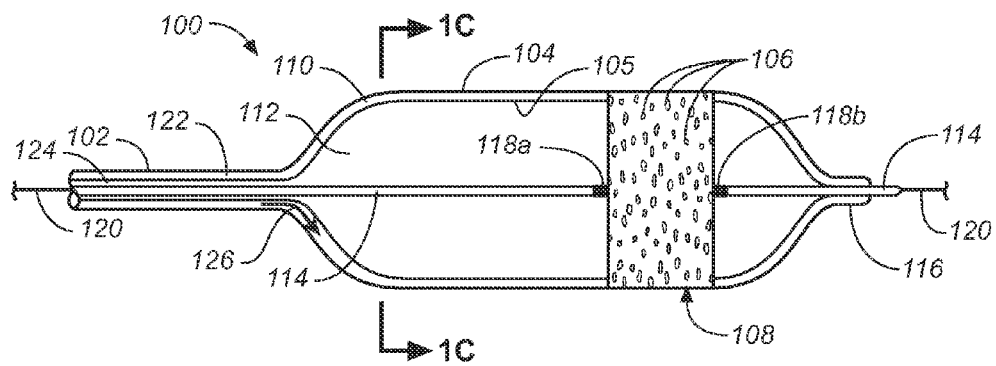
FIG. 1B illustrates the expandable sealant delivery apparatus of FIG. 1A in an expanded state suitable for further dilating an opening formed in graft material.
Figure 1C:
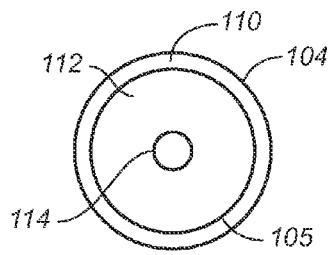
FIG. 1C is a sectional view of the expandable apparatus of FIG. 1B taken at 1C-1C.
Figure 1D:
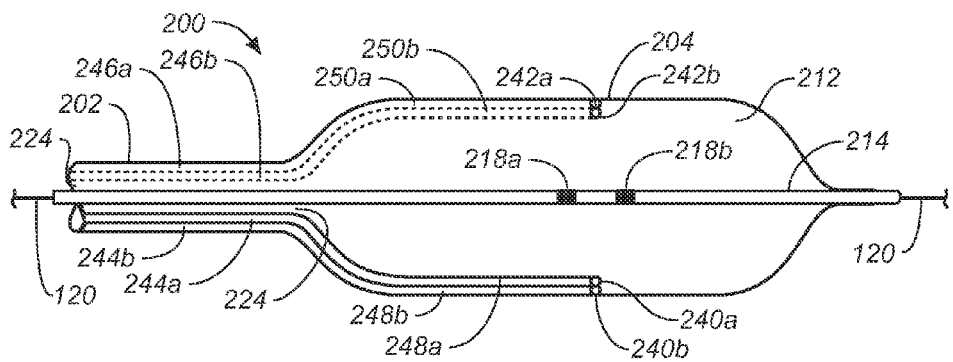
FIG. 1D illustrates another embodiment of expandable sealant delivery apparatus according to the invention in an inflated state with ports for delivery of a two part sealant (its uninflated profile is similar to that of apparatus 100 as depicted in FIG. 4A).

The diameter of the pores in the microporous membrane (e.g., 108) typically varies from about 2 microns to 500 microns depending on the sealant viscosity, and type of delivery apparatus used (e.g., whether it is a one part sealant delivery apparatus (see e.g., FIG. 1A) or multi-part sealant delivery apparatus (see e.g., FIG. 1D where pore size and sealant delivery tube size (I.D.—inner diameter) are approximately the same). Spacing between pores depends on pore size and the viscosity of the sealant. Generally speaking, when a larger pore size is used, the spacing between pores typically will be greater than when a smaller pore size is used. For example, micropores having a 250 micron diameter, can be spaced 1.5 mm apart in the embodiment illustrated in FIG. 1A. On the other hand, micropores having a 50 micron diameter, can be spaced 300 micron apart in the embodiment illustrated in FIG. 1A. When a higher viscosity sealant is used, a larger pore size (and larger sealant tube size (I.D.) in the embodiment of FIG. 1D) would be used with increased spacing between pores as compared to the configuration when lower viscosity sealant is used where smaller micropores (and smaller sealant tube size in the embodiment of FIG. 1D) would be used with relatively smaller spacing between micropores.

Referring to FIGS. 1A-C, an expandable sealant delivery apparatus is shown and generally designated with reference number 100. FIG. 1A shows apparatus 100 in a partially expanded or partially inflated state and FIG. 1B shows apparatus 100 in an expanded or inflated state.

Sealant delivery apparatus 100 comprises catheter 102 and expandable outer member or balloon 104, which is secured to the distal end of catheter 102 in any conventional manner. Balloon 104 comprises a membrane which has a plurality of micropores 106, which can be arranged in various configurations. In the illustrative embodiment, the micropores 106 are arranged or formed in the balloon membrane to form a 360 degree microporous band or cylindrical zone 108 through which sealant can be discharged. The micropores can be formed in expandable balloon 104 with any suitable means as is known in the art (microporous balloons currently are commercially available for applications such as drug delivery devices).

Referring to FIG. 1B, an inner expandable member or balloon 105 is provided within outer expandable balloon 104 to form sealant chamber 110 therebetween. Inner expandable balloon 105 forms an inflation chamber 112 in which inflation fluid can be introduced. In one embodiment, outer balloon 104 is compliant expandable material and inner balloon 105 is semi-compliant so that outer balloon 104 will expand with less pressure than inner balloon 105 or is less rigid than inner balloon 105. Examples of material that can be used to form outer balloon 104 include materials to which glue does not readily adhere such fluoropolymers including, but not limited to PTFE and polyethylene. One example of a suitable semi-compliant material that can be used to form inner expandable balloon 105 is nylon. A central tube (member, shaft) 114 containing a guidewire lumen for receiving a guidewire can be positioned within catheter 102 and the distal end of the expandable balloons secured with, for example, adhesive, to the distal end region of the central tube as diagramatically shown with reference numeral 116 in FIG. 1B. In one variation (not shown), the distal end of outer expandable balloon 104 terminates along the distal edge of microporous zone 108 and that distal edge is sealingly secured to the outer surface of inner balloon 105 with any suitable means such as adhesive. Radiopaque marker 118a can be secured to central tube 114 and aligned with or adjacent to the proximal end of microporous zone 108 and radiopaque marker 118b can be secured to central tube 114 and aligned with or adjacent to the distal end of microporous zone 108 to assist a surgeon in monitoring the location of microporous zone 108 and/or monitoring sealant flow from microporous zone 108 using conventional fluoroscopic techniques. In other variations, only one of the proximal or distal markers is used.

Catheter 102 includes a substantially annular channel 122 formed in its cylindrical wall and in fluid communication with sealant chamber 110 through which sealant is introduced into sealant chamber 110. Catheter 102 is sized so as to provide a pathway 124 between central tube 114 and the inner wall of the catheter through which inflation fluid can be introduced into inflation chamber 112.

In use, central tube 114 can be tracked over guidewire 120 to the desired site and inflation fluid such as a saline solution or a saline solution with contrast medium introduced into inflation chamber 112 and sealant 126 introduced into sealant chamber 110 for discharge through microporous zone 108. The inner expandable member 104 is slightly deflated before sealant is forced through the apparatus to provide sufficient space in sealant chamber 110. The saline solution with contrast medium variation facilitates monitoring balloon location with fluoroscopy.

Figure 4A:
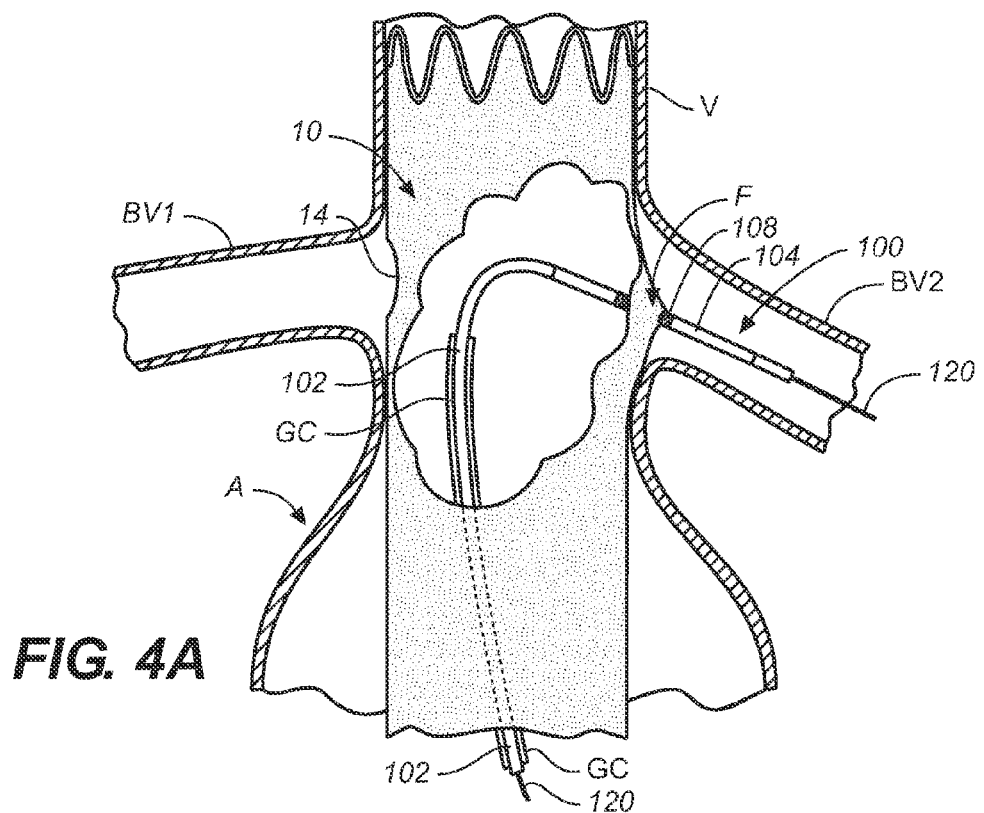
FIGS. 4A-D illustrate one example of the steps of a method of using the sealant delivery apparatus of FIG. 1 where

Referring to FIG. 1D, another embodiment of expandable sealant delivery apparatus according to the invention with ports for delivery of a two part sealant is shown in an inflated or expanded state and generally designated with reference numeral 200. Apparatus 200 has an uninflated profile similar to apparatus 100 as depicted in FIG. 4A. Sealant delivery apparatus 200 includes a catheter 202 and an expandable member or balloon 204, which can be formed from the same material from which expandable member or balloon 104 is made. Balloon 204 is secured to the distal end of catheter 202. Central tube 214 extends through catheter 202 and into balloon 204. The distal end of the balloon is secured to central tube 214 and the proximal end of the balloon secured to catheter 202 with any suitable means such as glue. Catheter 202 is sized so as to provide a pathway 224 between central tube 214 and the inner wall of the catheter through which inflation fluid can be introduced into inflation chamber 212, which balloon 204 forms.

In the illustrative example, balloon 204 is provided with two pairs of openings 240a,b and 242a,b (which can be micropores), the latter pair being spaced about 180 degrees from the former and shown in dashed line. Catheter 202 has formed therein channels 244a,b and 246a,b and balloon 204 includes channels 248a,b and 250a,b. Balloon channel 248a has one end fluidly coupled to catheter channel 244a and one end fluidly coupled to sealant outlet or micropore (240a). Balloon channel 248b has one end fluidly coupled to catheter channel 244b and one end fluidly coupled to sealant outlet or micropore 240b. Balloon channel 250a has one end fluidly coupled to catheter channel 246a and one end fluidly coupled to sealant outlet or micropore (242a). Balloon channel 250b has one end fluidly coupled to catheter channel 246b and one end fluidly coupled to sealant outlet or micropore (242b). The balloon channels can be formed by using a layer of material having the same composition as the balloon material or a different composition and fusing it to the inner surface of the balloon to create the channels. A single strip of material can be used to form each channel pair and a centerline therebetween welded to balloon 204 to form a channel pair. With this construction, a two part adhesive can be delivered where each part is delivered through one channel of a channel pair. In this manner, a first adhesive part or component can be introduced through channels 244a and 248a to exit from pore (240a) and second adhesive part or component can be introduced through channels 244b and 248b to exit from pore 240b and so forth. A separate container for each adhesive component is fluidly coupled to a respective component channel. For example, in a single outlet or micropore pair embodiment, a double barreled syringe can have a first barrel loaded with a first adhesive component and a second barrel loaded with a second adhesive component with the first barrel outlet coupled to channel 244a and the second barrel outlet coupled to channel 244b so that when the double barrel syringe plunger is actuated, it simultaneously delivers both components to balloon sealant outlets or openings 240a,b.

Although two pairs of sealant outlets or micropores are shown, one pair, two pair, three pair, four pair or more can be can be used. Typically, when two or more sealant outlet or micropore pairs are used, they will be symmetrically positioned about inflation chamber 212 in a circumferential direction as shown. Balloon 204 also can be rotated during sealant delivery to provide additional sealant distribution in a circumferential direction and/or to enhance mixing of the adhesive components. Alternatively, balloon 204 can be rotated after a first quantity of sealant is discharged at the target site and then another quantity of sealant discharged and that sequence repeated as desired. The diameter of the outlets or micropores and channels typically will be about 100 to 500 microns and typically the diameter of an outlet or micropore and its corresponding channel will be the same in the embodiment shown in FIG. 1D.

Radiopaque marker 218a can be secured to central tube 214 and aligned with or adjacent to the proximal side of the outlet or micropore pair or pairs and radiopaque marker 218b can be secured to central tube 214 and aligned with or adjacent to the distal end of the micropore pair or pairs to assist a surgeon in monitoring the location of the zone in which the outlets or micropores are arranged or monitoring sealant flow from the outlet or micropores zone using conventional fluoroscopic techniques. In other variations, only the proximal or distal marker is used.

Figure 1E:
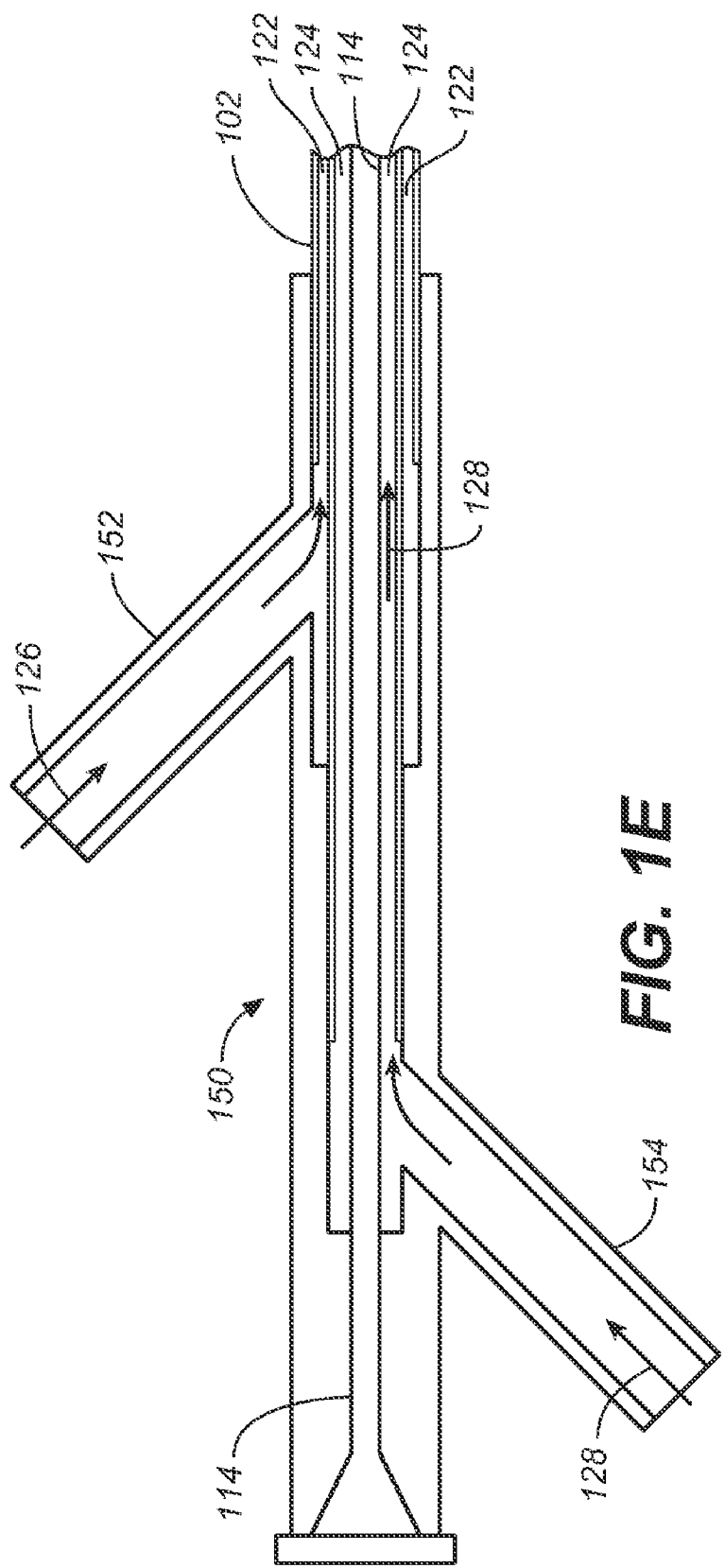
FIG. 1E is a diagrammatic partial sectional view of a Y-adapter suitable for delivering sealant and inflation fluids to the sealant delivery apparatus of FIG. 1A.

Referring to FIG. 1E, a Y-adapter suitable for delivering fluids to sealant delivery apparatus 100 is shown. Y-adapter 150 includes one inlet tube 152 to deliver sealant 126 to annular sealant channel 122 of sealant delivery apparatus catheter 102, which is disposed in a guide catheter (not shown), and another supply tube 154 to deliver inflation medium 128 to sealant delivery apparatus catheter 102 around central tube 114 and in inflation medium pathway 124.

Figures 1F, 1G:
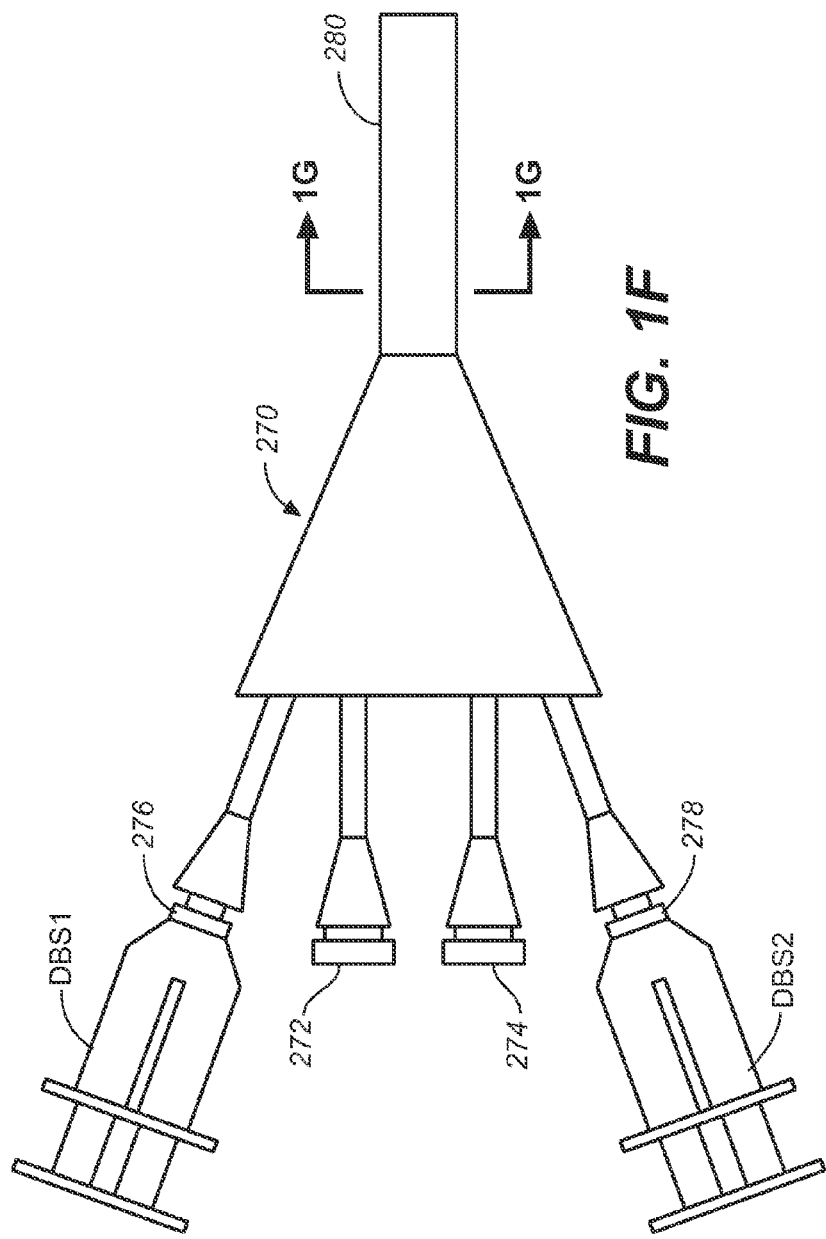
FIG. 1F illustrates a multi-branch Y-adapter suitable for delivering sealant and inflation fluids to the sealant delivery apparatus of FIG. 1D.
FIG. 1G is a sectional view taken at 1G-1G of FIG. 1F.

FIGS. 1F and 1G illustrate one example of a multi-branch Y-adapter, which is designated with numeral 270 and suitable for delivering sealant and inflation fluids to the sealant delivery apparatus 200. Y-adapter 270 includes inflation medium inlet port 272, guidewire inlet port 274, multi-channel sealant inlet port 276, multi-channel sealant inlet port 278 and outlet portion 280, which can be directly attached to the proximal end of sealant delivery apparatus catheter 202. Inlet port 272 includes or forms channel 272a, which extends through the Y-adapter and is coupled to catheter 202 to deliver inflation medium around central tube 214 in inflation medium pathway 224. Guidewire inlet port 274 includes or forms channel 274a which extends through the Y-adapter and is coupled to central tube 214 so that guidewire 120 can be introduced into channel 274a and then through guidewire lumen of central tube 214 which extends through catheter 202. In sum, channel 272a provides means for delivering inflation medium to inflation medium pathway 224 in sealant delivery apparatus 200 and channel 274a provides means for delivering a guidewire to guidewire lumen of central tube 214. Multi-channel sealant inlet port 276 includes separate channels 276a,b, which extend through the Y-connector and are fluidly coupled to sealant delivery channels 244a,b, which are fluidly coupled to openings 240a,b. Multi-channel sealant inlet port 278 includes separate channels 278a,b, which extend through the Y-connector and are fluidly coupled to sealant delivery channels 246a,b, which are fluidly coupled to openings 242a,b. In this manner, sealant inlet ports 276 and 278 provide means for introducing two part sealant into channels 276a,b and 278a,b, which provide means for delivery of first and second adhesive components in separate channels to sealant delivery apparatus opening or outlet pairs 240a,b and 242a,b. Referring to FIG. 1F, exemplary double barreled syringes DBS1 and DBS2 are diagrammatically shown coupled to inlet ports 276 and 278. In this manner each of the two outlets of each double barrel syringe can be connected to one channel of a channel pair 276a,b and 278a,b so that actuation of either of the double barrel syringe plungers simultaneously delivers both adhesive components in the actuated syringe to the balloon in parallel. The plungers can be actuated at the same time or sequentially.

Figure 2A:
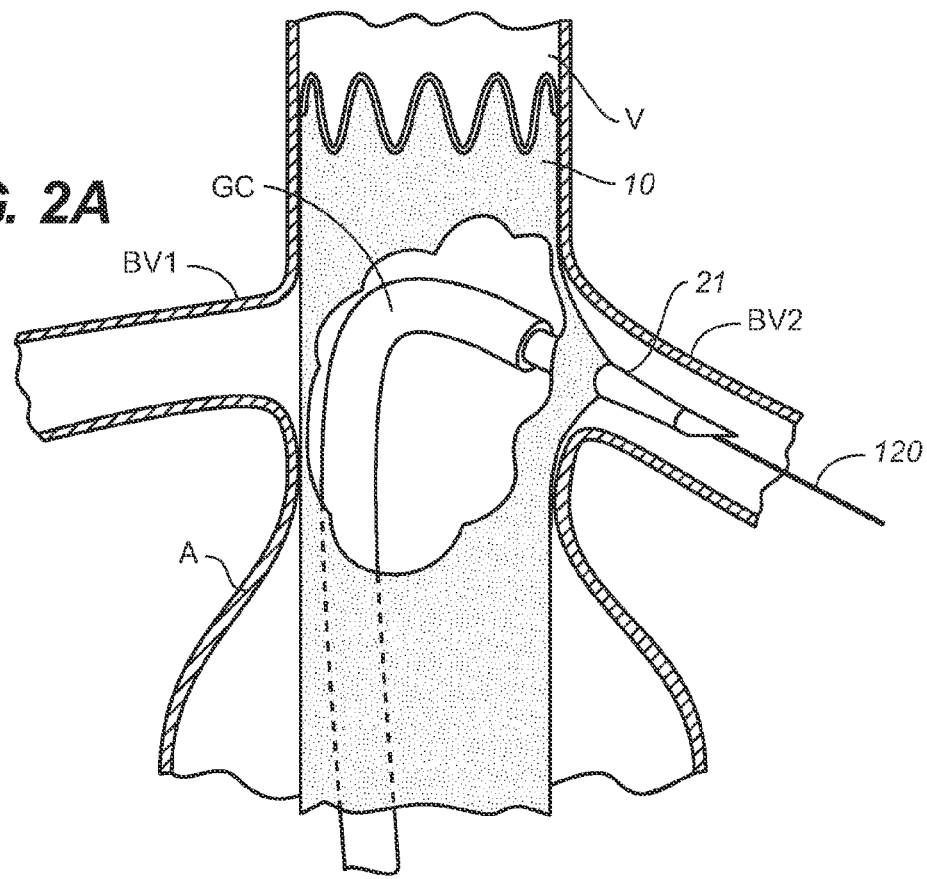
FIG. 2A illustrates a conventional puncture catheter forming a side opening in a stent-graft positioned in a vessel covering a branch vessel.
Figure 2B:
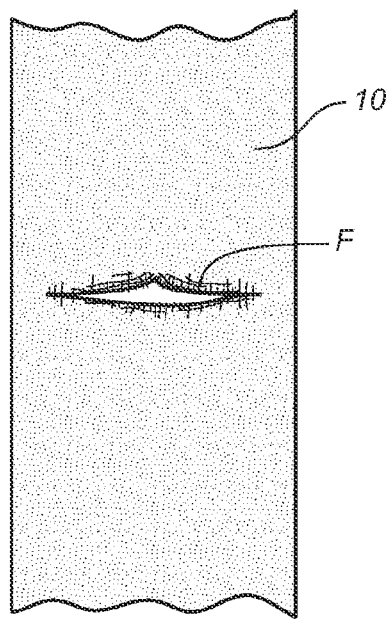
FIG. 2B illustrates an opening formed with a puncture catheter in the cover or cloth of a stent-graft such as the stent-graft illustrated in FIG. 2A.
Figure 3:
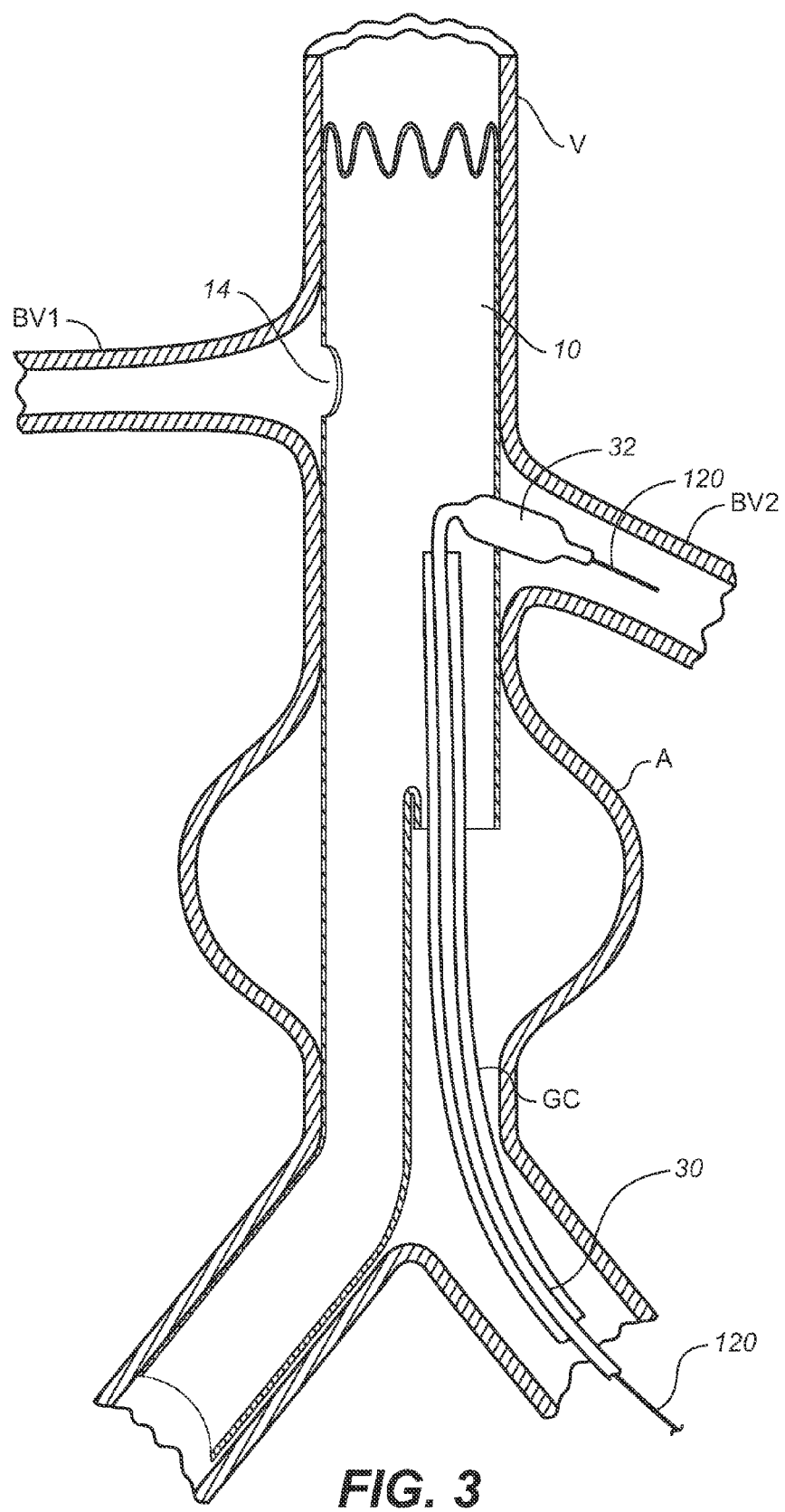
FIG. 3 illustrates the branch vessel of FIG. 2A with a conventional angioplasty balloon catheter delivered over the guidewire and positioned in the opening in the stent-graft that was formed with the puncture catheter, wherein the puncture catheter has been withdrawn and the guidewire, which was used to deliver the puncture catheter to the puncture site and then extended through the puncture, was left with its distal end extending into the branch vessel.

Referring to FIGS. 2A-B, 3, and 4A-D, a method of creating a fenestration in vivo and then using the sealing apparatus of FIG. 1A will be described. Referring to FIG. 2A, a conventional hollow puncture needle 21 is delivered through guide catheter "GC," which can be a steerable guide catheter, and the sharp distal tip of the needle passed through the wall of the stent-graft 10 to form an opening in graft material of the stent-graft adjacent to a branch vessel "BV2." As shown in FIG. 2A, the puncture needle has a tapered distal portion, which dilates the punctured opening. In this example, the stent-graft is shown positioned in vessel "V" so as to bypass aneurysm "A," which can be an abdominal aortic aneurysm, and could extend above branch vessels "BV1" and "BV2," which can be the renal arteries. Guidewire 120 is extended out from puncture needle 21 and the puncture needle retracted, while leaving the guidewire in place. An example, of an opening or fenestration "F" formed in the graft material of stent-graft 10 with puncture needle 21 is shown in FIG. 2B. Referring to FIG. 3, a conventional angioplasty catheter 30 is delivered through guide catheter "GC" and guided over guidewire 120 so that its balloon 32 is positioned in fenestration "F" where it is partially inflated to partially dilate the fenestration or opening formed in situ as shown in FIG. 3. The angioplasty catheter is then removed. If stent-graft 10 is not initially provided with opening 14 to align with branch vessel "BV1," an opening can be formed in stent-graft 10 in vivo adjacent to branch vessel "BV1 " in a similar manner to that described above. The puncture catheter would be used to provide a puncture at each branch vessel site and then the angioplasty catheter used to partially dilate the punctured openings.

Although an exemplary puncture needle is shown in FIG. 2A to form an opening in the stent-graft, other known puncture devices can be used in any of the procedures described herein where a puncture is made in a stent-graft. Further, the devices disclosed in U.S. patent application Ser. No. 12/106677, which discloses an RF plasma electrode puncture device and U.S. patent application Ser. No. 11/939,106, filed on 13 Nov. 2007, which discloses a hybrid needle dilator can be used, the disclosures of which are hereby incorporated herein by reference thereto.

Figure 4B:
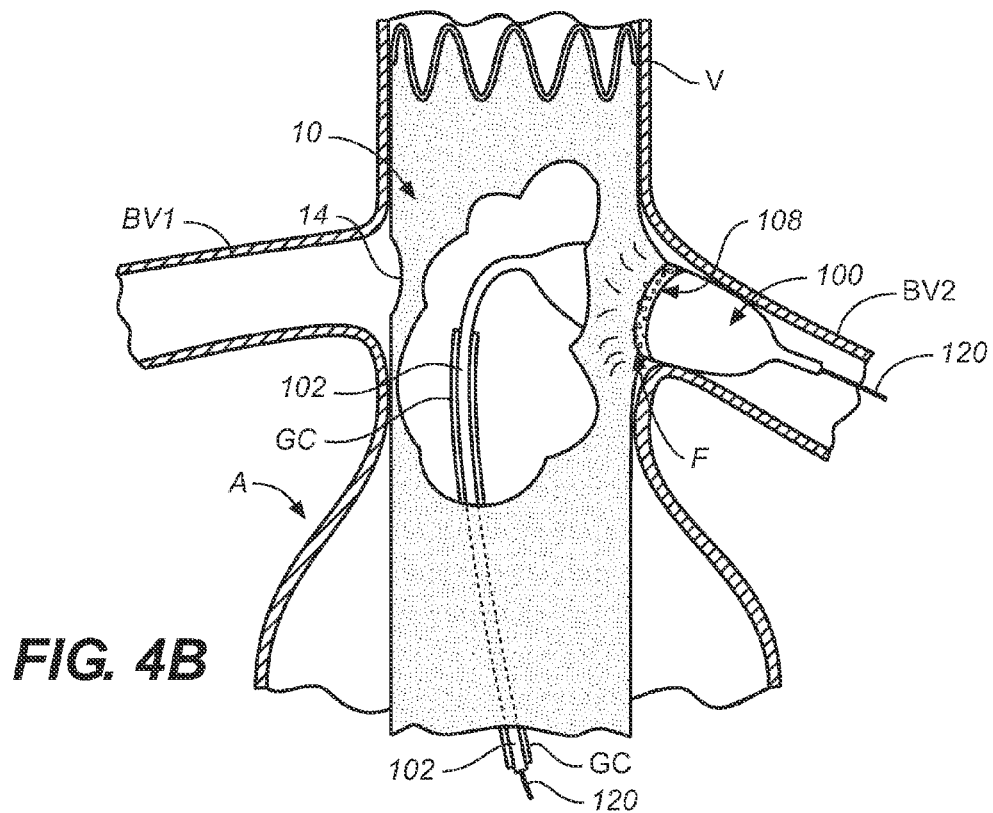

Referring to FIG. 4A, sealant delivery catheter 100 is delivered over guidewire 120 and through guide catheter "GC" and is positioned with the marginal portion of the graft material that surrounds fenestration "F" surrounding microporous zone 108. Inflation medium is introduced into inner balloon 105 (FIG. 1B) to further dilate the fenestration or opening. The inflation medium pressure is then reduced to allow inner balloon 105 (FIG. 1B) to slightly deflate and allow sealant to more readily pass into sealant chamber 110. Sealant is then introduced under pressure into sealant chamber 110. Thereafter, inner balloon 105 is inflated to assist the sealant in passing through microporous zone 108 to the graft material (e.g., cloth material) surrounding the fenestration or opening (FIG. 4B). Using sealant with contrast medium as described herein facilitates visual monitoring of adhesive in chamber 110.

Figure 4C:
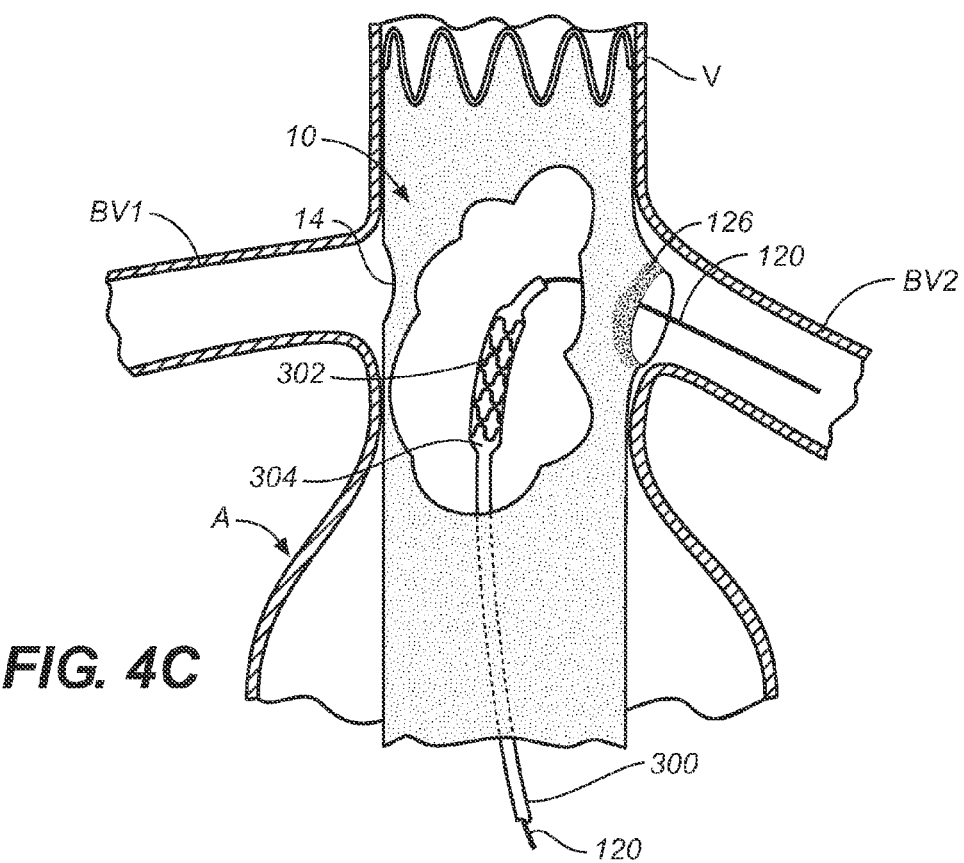
Figure 4D:
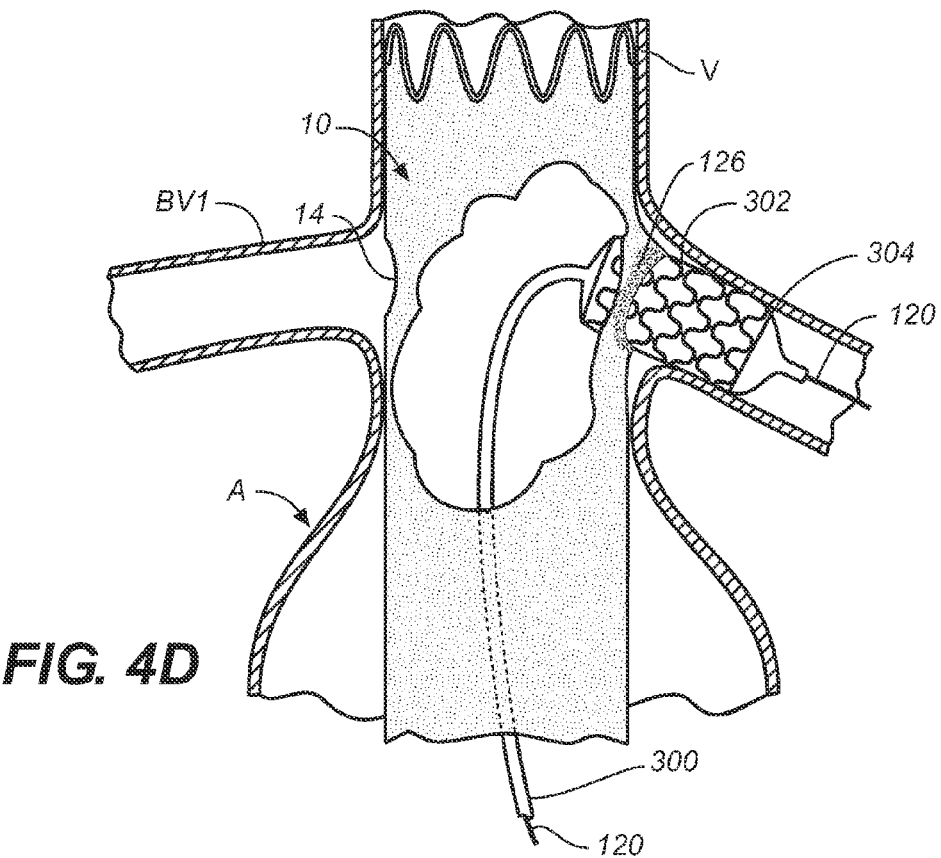

The sealant delivery apparatus is deflated and drawn into guide catheter "GC" and then both the sealant delivery apparatus and guide catheter are withdrawn while leaving guidewire 120 in place to deliver a branch vessel stent-graft (FIG. 4C). A conventional balloon expanding stent-graft delivery catheter 300 is delivered over guidewire 120 and stent-graft 302, which is mounted on balloon 304 positioned in the branch vessel "BV1." Balloon 304 is radially expanded so that it pushes the stent-graft into the adhesive material that surrounds the fenestration FIG. 4D. Balloon 304 is deflated and stent-graft catheter 300 and guide wire 120 removed. Although a balloon expandable branch vessel stent-graft has been described, a self-expanding stent-graft can be used. As the stent is deployed, it completes the dilation of the fenestration or opening. The adhesive material partially or completely fills the area between the branch vessel stent-graft and the edges of the stent-graft fenestration.

Figure 5A:
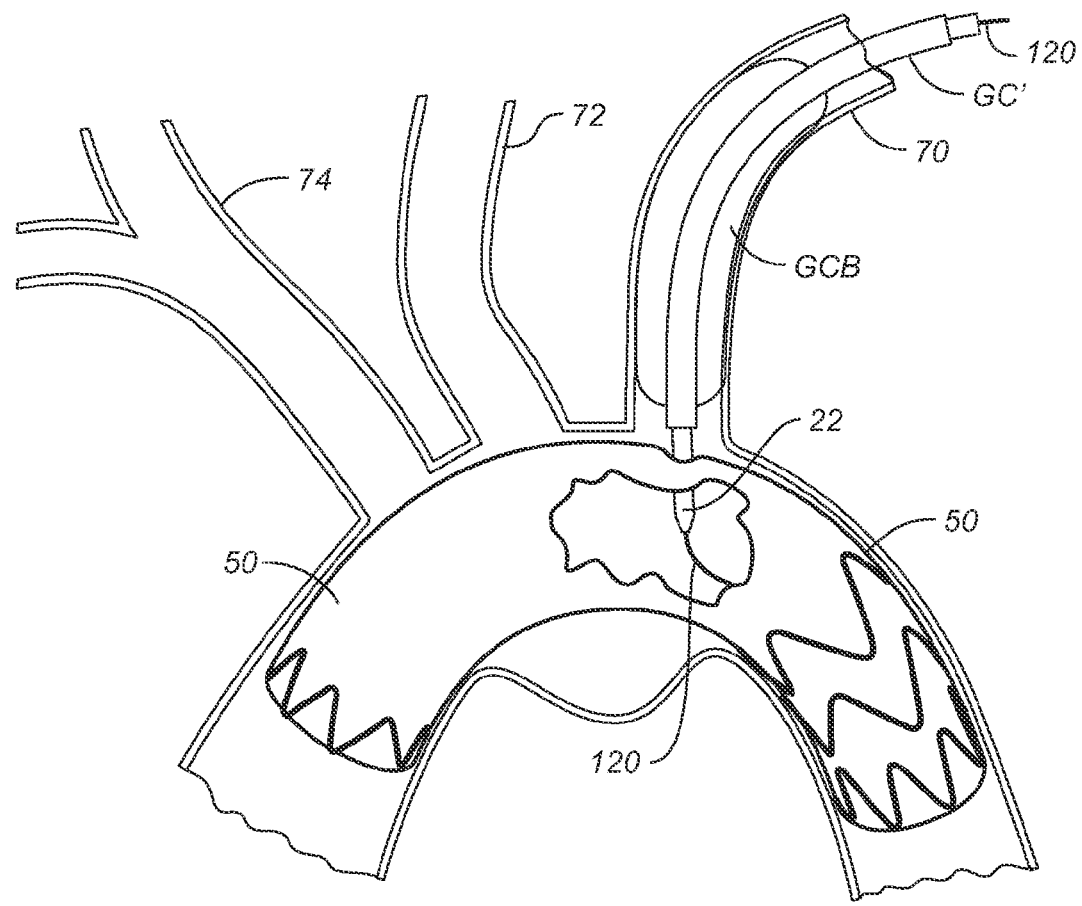
FIG. 5A-E illustrate another method according to the invention where the sealant delivery device of FIG. 1A is delivered through the subclavian artery to an opening in a stent-graft positioned in a patient's aorta below the subclavian artery, where

Referring to FIGS. 5A-E, use of apparatus 100 in a thoracic procedure will be described. Referring to FIG. 5A, a main stent-graft 50 has been delivered to the aorta below and covering the ostia of the left subclavian artery 70, the common carotid artery 72, and the brachiocephalic artery 74. Guide catheter "GC'," which has a guide catheter centering balloon "GCB" and can be a steerable guide catheter, is delivered through the left subclavian artery such that the distal end of the guide catheter contacts or is adjacent to stent-graft 50. Guide catheter "GC'" can be used to deliver a conventional puncture device, which includes a needle (hidden from view) and dilator 22 in which the needle is slidably mounted so that it can be extended therefrom. Guide catheter balloon "GCB" is expanded to center guide catheter "GC'" and the puncture device, and the needle extended from the dilator and passed through the wall of the graft material of stent-graft 50 followed by dilator 22. After the needle is passed through the graft material, guidewire 120 is passed through the needle, which is a hollow needle, and through the opening or puncture formed in the graft material. The needle is retracted from the stent-graft and into the guide catheter, and dilator 22 advanced to dilate the puncture or opening as diagrammatically shown in FIG. 5A. The dilator is then retracted inside guide catheter "GC'" after which the puncture device is removed from the guide catheter. Guide catheter balloon "GCB" is deflated and the guide catheter partially retracted. An angioplasty balloon (not shown) is delivered through the guide catheter over guidewire 120, positioned in the opening, and partially dilated to form an opening of desired size in the stent-graft wall in a manner similar to that shown in FIG. 3.

Figure 5B:
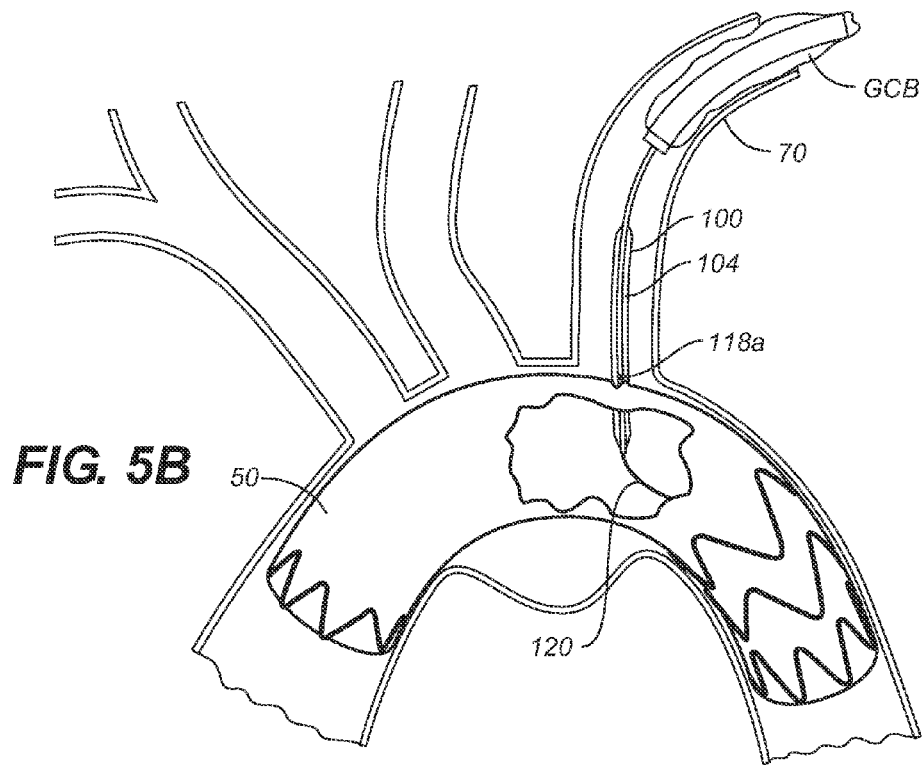

Referring to FIG. 5B, sealant delivery apparatus 100 is delivered over guidewire 120 and through guide catheter "GC'." The sealant delivery apparatus is positioned using fluoroscopy to position radiopaque marker 118a above the openings as shown, for example, in FIG. 5B to align microporous zone 108 with the opening formed in the stent-graft wall.

Figure 5C:
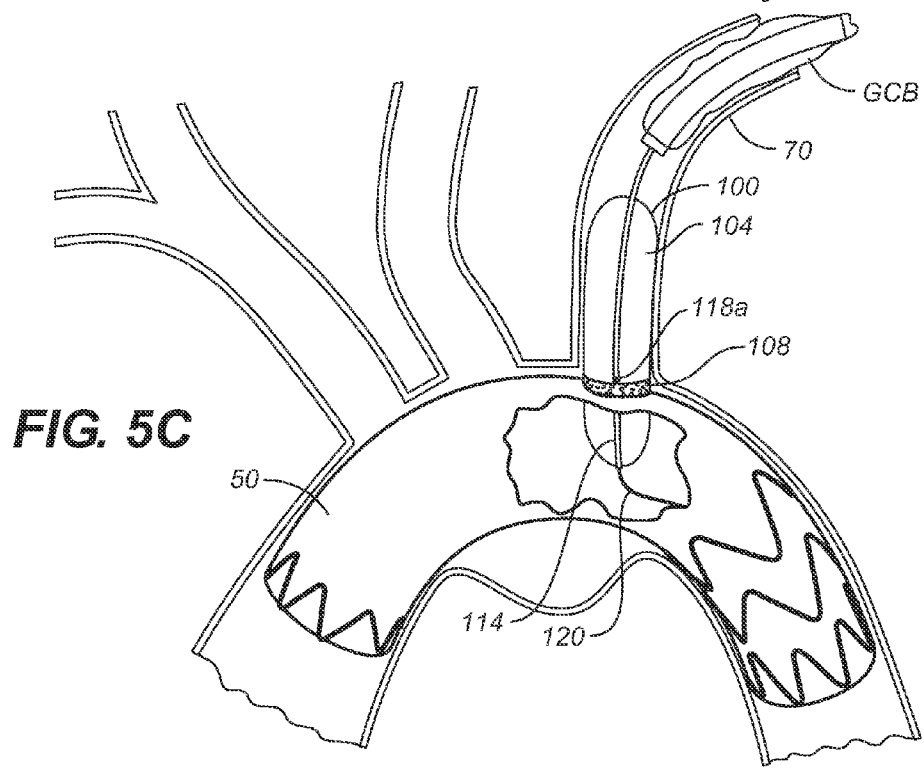

Referring to FIG. 5C, inner balloon 105 is partially radially expanded, which radially expands outer balloon 104, to further dilate the opening in the stent-graft wall. The inner balloon is then slightly deflated and sealant 126 delivered to sealant chamber 110. Thereafter, inner balloon 105 is inflated to assist the sealant in passing through micropores 106 of microporous zone 108 and into the stent-graft graft material. Using sealant with contrast medium as described herein facilitates visual monitoring of adhesive in chamber 110.

Figure 5D:
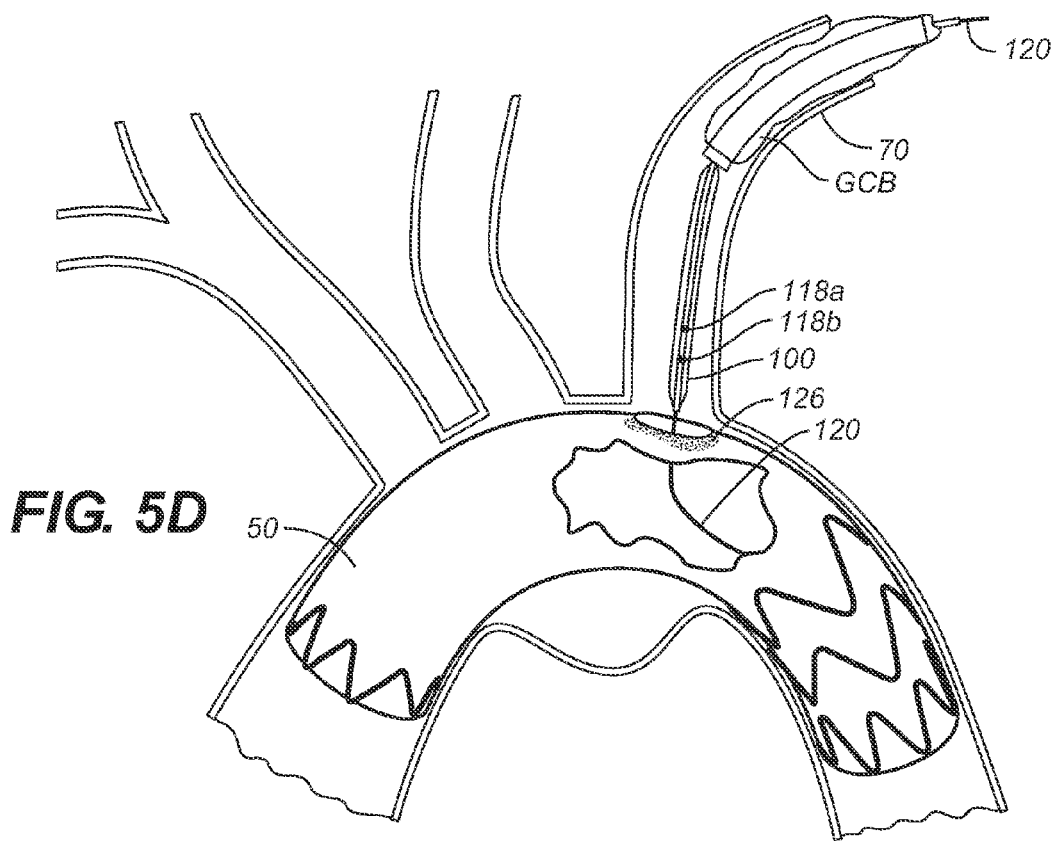
Figure 5E:
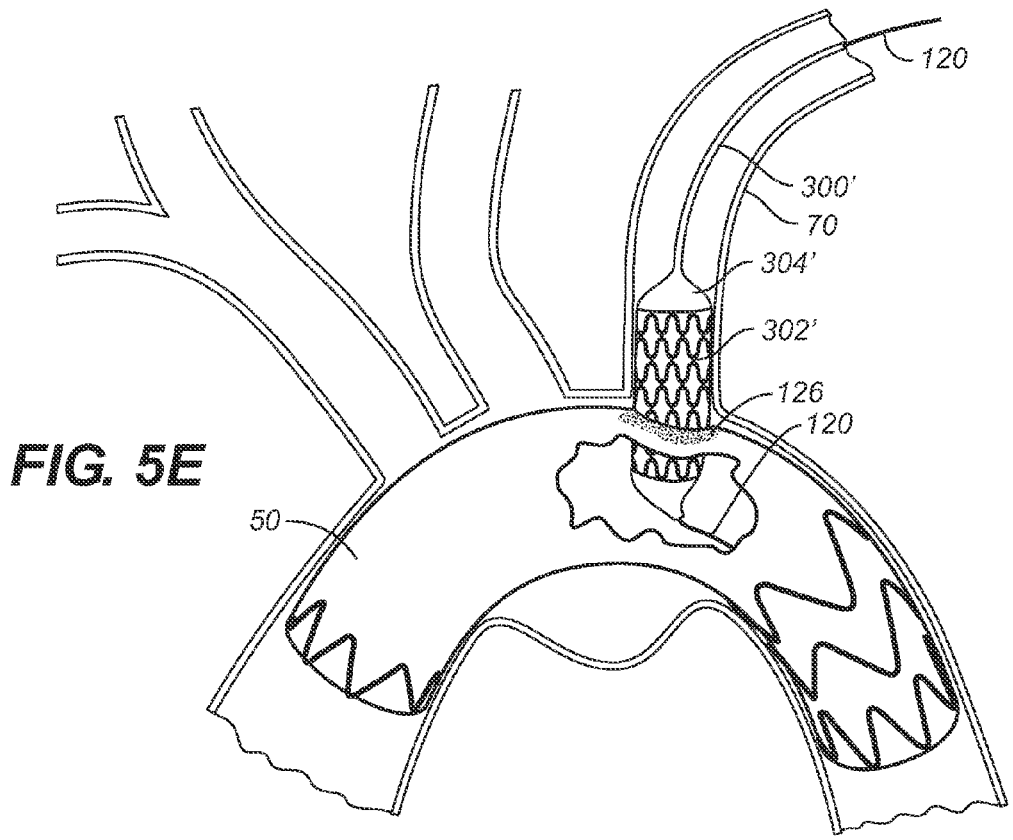

Referring to FIG. 5D, the sealant delivery apparatus balloons are deflated and the sealant delivery apparatus retracted inside guide catheter "GC'" and the apparatus and guide catheter removed while leaving guidewire 120 in place. Stent-graft delivery catheter 300' is then delivered over guidewire 120, balloon expandable stent-graft 302' positioned in the opening in stent-graft 50, and balloon 304' expanded to secure the stent-graft in position (FIG. 5E). Balloon 304' is deflated and stent-graft catheter 300' and the guidewire removed. Although a balloon expandable branch vessel stent-graft has been described, a self-expanding stent-graft can be used.

Sealant delivery apparatus 200 can be used in the examples described above in the same manner as sealant delivery apparatus 100 with the exception that two part sealant is delivered and the apparatus can be rotated to mix the sealant components and/or further circumferentially distribute the sealant depending on the number of micropore pairs used. Further, since there is only a single balloon as compared to the dual balloon construction of sealant apparatus 100, the balloon need not be deflated prior to sealant delivery. Balloon 204 is simply positioned and inflated to further dilate the fenestration or opening after which sealant delivered is delivered therefrom.

In another embodiment, sealant delivery apparatus 100 or 200 can be used to seal two stent-grafts together. In one example, the apparatus can be used to seal the contralateral iliac leg to the main body of a bifurcated stent-graft. This can be done, for example, to repair a leak at the juncture of these elements. An example will be described below with reference to FIG. 8. The seal also may prevent migration of the contralateral leg. In this embodiment, the end portion of the inner graft may be selected to be more porous than the outer graft material in the overlapping region of the two graft members so as to enhance sealant passage through the inner graft to the outer graft in that region. The sealing adhesive is likely to be applied where a gap between the stent grafts can be filled and sealed.

Figure 6:
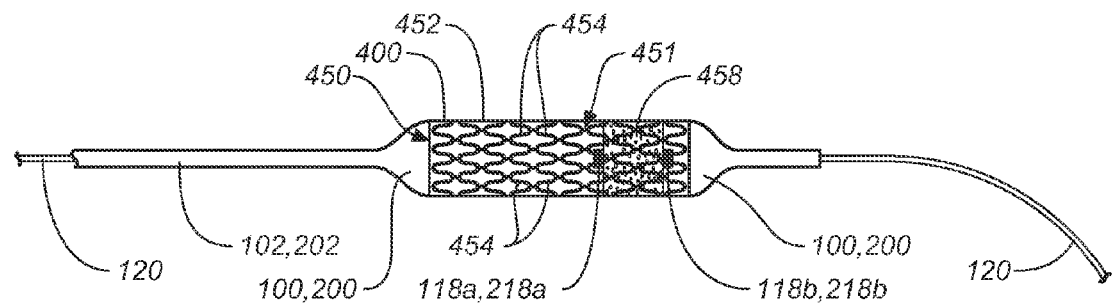
FIG. 6 illustrates another sealant delivery apparatus embodiment according to the invention.

Referring to FIG. 6, another sealant delivery apparatus embodiment according to the invention is shown in an inflated or expanded state and generally designated with reference numeral 400. Sealant delivery apparatus 400 is the same as sealant delivery apparatus 100 or 200 with the addition of stent-graft (or covered stent) 450 mounted around the balloon (balloon 104 or 204, depending on whether sealant delivery apparatus 100 or 200 is combined therewith) and has an uninflated or unexpanded profile similar to that shown in FIG. 4A in connection with apparatus 100. In the illustrative embodiment, stent-graft 450 includes tubular graft 452 and a stent 451, which comprises interconnected undulating stent rings 454, coupled thereto. Stent-grafts 302 and 302' described above can have a similar stent structure. However, it should be understood that other stent configurations can be used as well. Tubular graft 452 includes a microporous zone 458 aligned with the microporous zone or sealant outlets of either delivery apparatus 100 or 200 depending on which apparatus is used (the microporous zone or sealant outlets are beneath microporous zone 458 and hidden from view). When tubular graft 452 is PTFE or polyester, the pore size can be controlled during manufacture of the graft. When the tubular graft is polyester, multiple sections can be used. For example, a microporous section for sealant delivery can be coupled or attached to a non-microporous section. In the embodiment illustrated in FIG. 6, stent 451 extends over microporous zone 458. In one alternative embodiment, the stent does not extend over microporous zone 458.

Figure 7A:
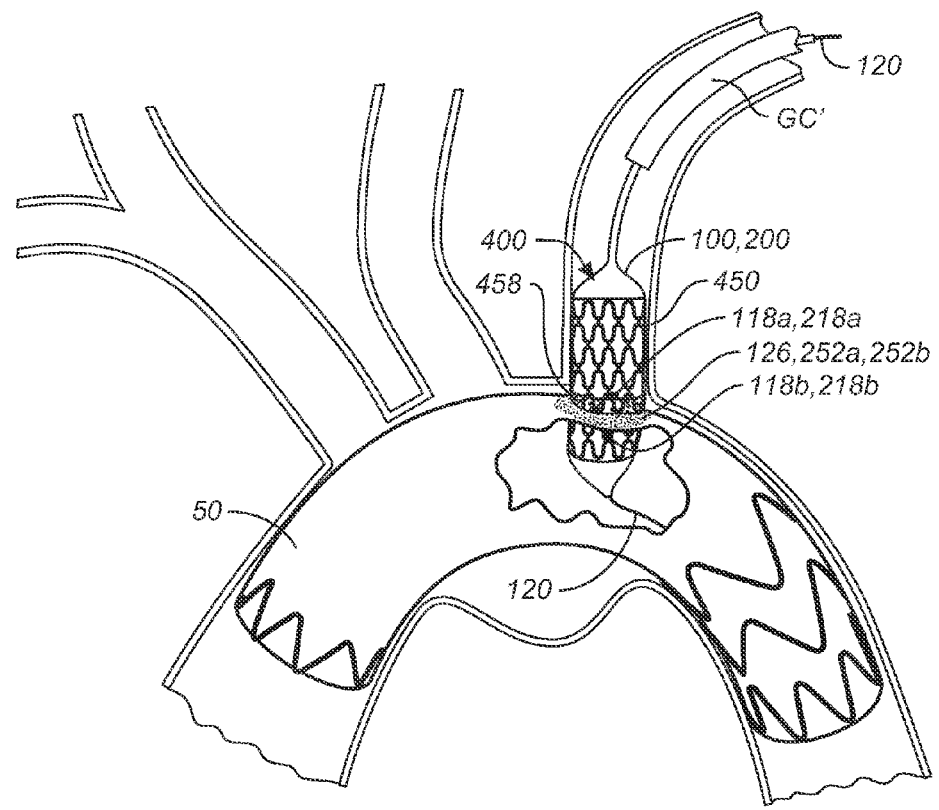
FIG. 7A illustrates use of the stent-graft carrying sealant delivery apparatus of FIG. 6 in a thoracic aorta application as depicted in FIG. 5A.

Referring to FIG. 7A, one method of using sealant delivery apparatus 400 is shown where sealant delivery apparatus 400 is tracked over guidewire 120 through guide catheter "GC" and subclavian artery 70 to a puncture or hole formed in vivo in stent-graft 50 using any of the approaches described above. Radiopaque markers 118a,b or 218a,b are used to position microporous zone 458 at the desired location using fluoroscopy in a manner similar to that described above. Expandable balloon 105 or 204 is expanded to expand and deploy stent-graft 450 and then sealant is delivered through the micropores or sealant outlets of either balloon 104 or 204 according to the steps described above after which it passes through to microporous zone 458 and into to stent-graft 50 graft material, which surrounds the puncture. When using sealant apparatus 100 in combination with stent-graft 450, stent-graft 450 is expanded and deployed by inflating inner expandable balloon 105 with saline solution or saline solution with contrast medium. Pressure in the balloon lumen is slightly reduced and sealant is injected into the sealant chamber 110. Thereafter, inner balloon 105 is inflated to assist the sealant in passing through microporous zones 108 and 458 and into the graft material surrounding the fenestration or opening in which stent-graft 450 is placed. Using sealant with contrast medium as described herein facilitates visual monitoring of adhesive in chamber 110. If the sealant comprises two components they are delivered through two separate lumens as described with reference to FIG. 1D. After the sealant is delivered, the sealant delivery apparatus balloon (when apparatus 200 is used) or balloons (when apparatus 100 is used) are deflated and withdrawn into the guide catheter. As in all of the embodiments described herein, the guide catheter can form a barrier between the blood and the sealant remaining on the sealant delivery apparatus when the latter is withdrawn therethrough. Sealant delivery apparatus 400 eliminates the separate balloon and sealant delivery step as it combines the sealant delivery apparatus with the balloon expandable stent-graft.

Figure 7B:
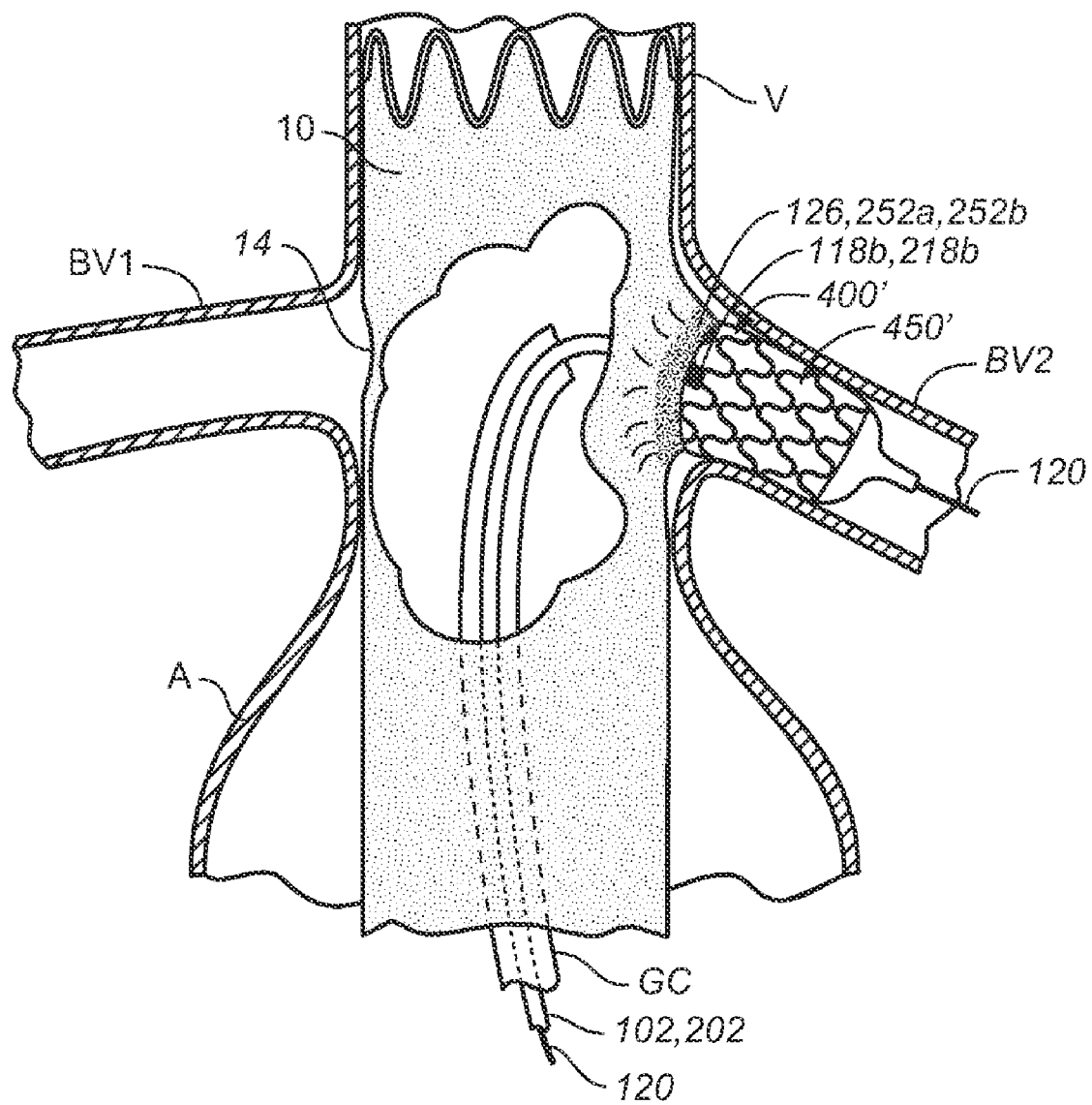
FIG. 7B illustrates use of the stent-graft carrying sealant delivery apparatus of FIG. 6 in an abdominal aortic application as depicted in FIG. 2A.

Referring to FIG. 7B, another method is shown using sealant delivery apparatus 400' at a puncture site in stent-graft 10 adjacent to a branch vessel "BV2," which corresponds to the site depicted in FIG. 2A. Stent-graft delivery apparatus 400' is the same as stent-graft delivery apparatus 400 (including their stent constructions) with the exception that the microporous zones (hidden form view) in the balloon and graft material of stent-graft 450' are closer to the proximal end of the expandable portion of the apparatus to adapt to this application where the apparatus passes from the aorta to a branch vessel as compared to the embodiment illustrated in FIG. 7A where the apparatus passes from a branch vessel to the aorta. Stent-graft 450' is sized for this particular application and sealant delivery apparatus 400' is operated as described above.

Figure 8:
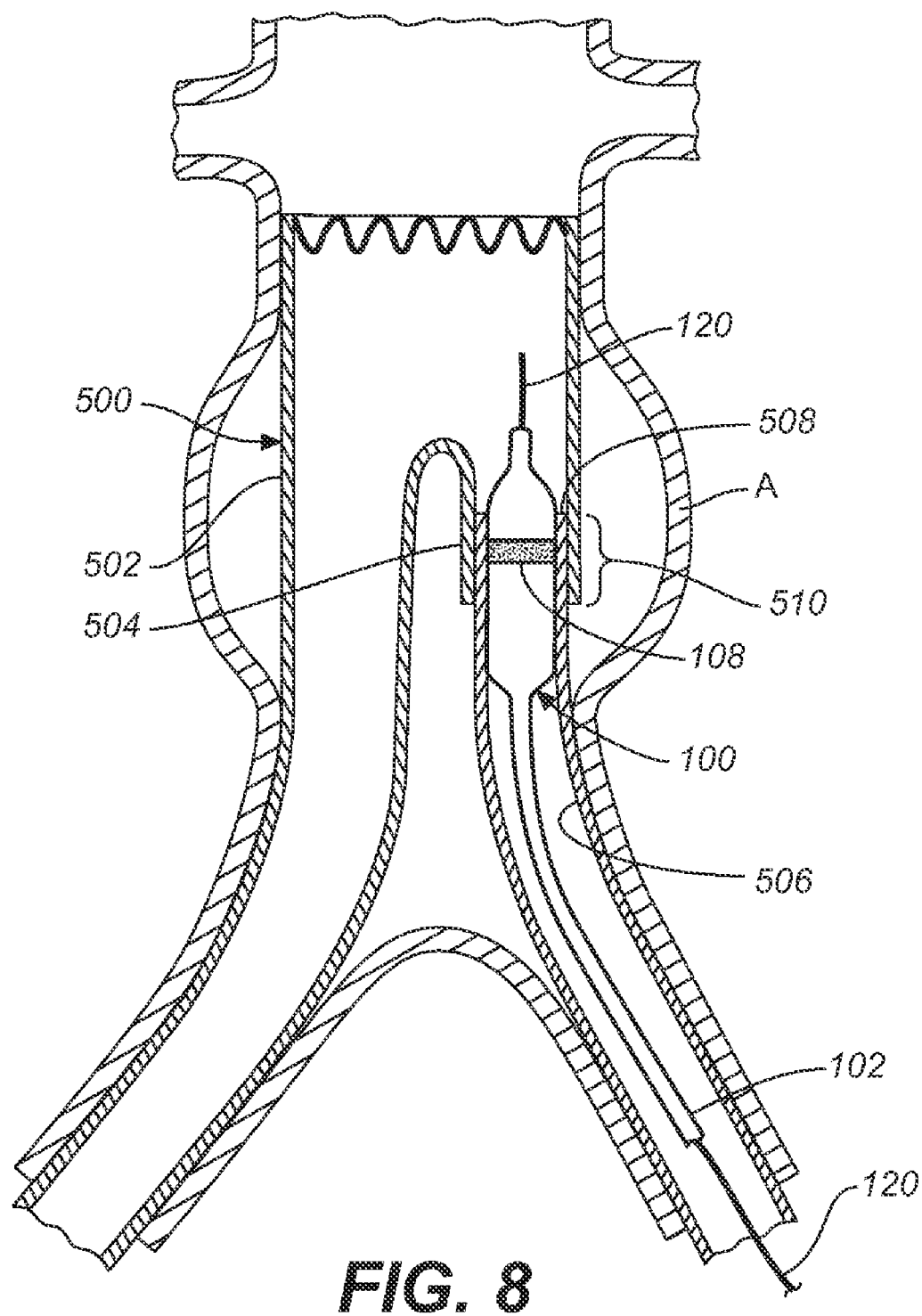
FIG. 8 diagrammatically illustrates sealing overlapping portions of stent-grafts using the apparatus of FIGS. 1A or 1D.

Referring to FIG. 8, sealant delivery apparatus 100 is shown sealing together two stent-grafts, which form a bifurcated stent-graft 500. Bifurcated stent-graft 500 includes main body component (portion) 502 with a short leg 504. Contralateral iliac leg 506 has one end 508 positioned inside short leg 504 such that the short leg 504 overlaps contralateral leg 506 along overlap portion 510 of contralateral leg 506. Microporous zone 108 is aligned with overlap portion 510, the inner balloon 105 partially expanded and then sealant delivered through microporous zone 108 and overlap portion 510 to create a 3600 ring of adhesive bonding legs 504 and 506 together. Although sealant delivery apparatus 100 is shown, sealant delivery apparatus 200 alternatively can be used. When sealant delivery apparatus 200 is used, the pore pair or pairs (e.g., pores 240a,b and 242a,b) are aligned with overlap portion 510, balloon 204 is expanded to engage the inner wall of contralateral iliac leg 506 and apply a radial force thereagainst, and sealant delivered through overlap portion 510 as the balloon is rotated to create a 360° ring of adhesive bonding legs 504 and 506 together. The apparatus is then removed. In this procedure a fast curing adhesive typically is used. Further, the graft material forming overlap portion 510 of contralateral leg stent-graft 506, which extends into short leg 504 may be made sufficiently porous so as to allow the sealant to pass therethrough. As would be apparent to one of ordinary skill, overlap portion 510 can have a length less the entire length of the contralateral leg that is inserted into short leg 504. The remainder of the graft material of contralateral leg stent-graft 506 is conventional material suitable for providing a barrier to blood flow therethrough. Stent-graft 500 can have a plurality of undulating stent rings (not shown), which are not interconnected with bridge elements as compared to interconnected stent rings 454. This stent construction is well known in the art. Such stent rings can be attached to the inner or outer surface of main body portion 502, short leg 504, contralateral leg 506, and the ipsilateral leg as is known in the art. An optional support spring as shown can be provided at the upper end of the stent-graft to provide radial strength. It can be positioned on the interior or exterior of the graft and secured thereto with conventional means. Another support spring also can be provided at the ends of the stent-graft legs if desired. An undulating bare spring wire also can be attached with conventional means to the upper end of the stent-graft to extend above the stent-graft as is known in the art to enhance fixation. One or more end support rings as described above also can be provided in stent-grafts 302, 302', 450, or 450' as well. Stent-graft 10 also can incorporate a stent construction with separate undulating stent rings as described above in connection with stent-graft 500.

Any feature described in any one embodiment described herein can be combined with any other feature or features of any of the other embodiments or features described herein. Furthermore, variations and modifications of the devices and methods disclosed herein will be readily apparent to persons skilled in the art.

What is claimed is:

1. Endolumenal sealant delivery apparatus for delivering sealant in a lumen of a human body comprising:
   a catheter;
   an expandable balloon having a region having a plurality of micropores adapted to allow surgical sealant to pass therethrough; said expandable balloon being coupled to said catheter; and a graft surrounding at least a portion of said expandable balloon, which has a region with a plurality of micropores, said graft having a region including a plurality of micropores aligned with said expandable balloon region having a plurality of micropores.

2. The apparatus of claim 1, further including an inner expandable balloon, said expandable balloon, which has a region with a plurality of micropores, surrounding at least a portion of said inner balloon to form a sealant chamber therebetween.

3. The apparatus of claim 2, wherein said inner balloon forms an inner chamber and said catheter includes a lumen fluidly coupled to said inner chamber for delivering fluid to said inner chamber to expand said inner expandable balloon, said catheter further including a sealant lumen fluidly coupled to the sealant chamber formed between said balloons.

4. The apparatus of claim 2, wherein said inner expandable balloon is formed from semi-compliant material and said expandable balloon that surrounds at least a portion of the inner balloon to form a sealant chamber therebetween is formed from compliant material.

5. The apparatus of claim 2, further including a central tube extending through said catheter and in within said inner expandable balloon, wherein each balloon has a distal end and a proximal end, said distal ends being coupled to said central tube and said proximal ends being coupled to said catheter.

6. The apparatus of claim 2, wherein said inner expandable balloon encapsulates said expandable balloon.

7. The apparatus of claim 2, wherein said pores have a diameter in a range of about 2microns to about 500 microns.

8. The apparatus of claim 1, further including first and second radiopaque markers, wherein said region, which has a plurality of micropores, has a distal end and a proximal end, said first radiopaque marker being positioned adjacent to said proximal end and said second radiopaque marker being positioned adjacent to said distal end.

9. The apparatus of claim 8, further including a central tube extending through said catheter and within said expandable balloon, said markers being coupled to said central tube.

10. The apparatus of claim 1, wherein said region, which has a plurality of micropores, forms a 360 degree band.

11. The apparatus of claim 10, wherein said region, which has a plurality of micropores, is cylindrical.

12. Endolumenal sealant delivery apparatus for delivering sealant in a lumen of a human body comprising:
a catheter;
an expandable balloon having a region having a plurality of micropores adapted to allow surgical sealant to pass therethrough; said expandable balloon being coupled to said catheter; and
a stent-graft surrounding at least a portion of said expandable balloon, which has a region with a plurality of micropores, the stent-graft having a region including a plurality of micropores aligned with said expandable balloon region having a plurality of micropores.

13. The apparatus of claim 12, further including an inner expandable balloon, said expandable balloon, which has a region with a plurality of micropores, surrounding at least a portion of said inner balloon to form a sealant chamber therebetween.

14. The apparatus of claim 13, wherein said inner balloon forms an inner chamber and said catheter includes a lumen fluidly coupled to said inner chamber for delivering fluid to said inner chamber to expand said inner expandable balloon, said catheter further including a sealant lumen fluidly coupled to the sealant chamber formed between said balloons.

15. The apparatus of claim 13, wherein said inner expandable balloon is formed from semi-compliant material and said expandable balloon that surrounds at least a portion of the inner balloon to form a sealant chamber therebetween is formed from compliant material.

16. The apparatus of claim 13, further including a central tube extending through said catheter and in within said inner expandable balloon, wherein each balloon has a distal end and a proximal end, said distal ends being coupled to said central tube and said proximal ends being coupled to said catheter.

17. The apparatus of claim 13, wherein said inner expandable balloon encapsulates said expandable balloon.

18. The apparatus of claim 13, wherein said pores have a diameter in a range of about 2microns to about 500 microns.

19. The apparatus of claim 12, further including first and second radiopaque markers, wherein said region, which has a plurality of micropores, has a distal end and a proximal end, said first radiopaque marker being positioned adjacent to said proximal end and said second radiopaque marker being positioned adjacent to said distal end.

20. The apparatus of claim 19, further including a central tube extending through said catheter and within said expandable balloon, said markers being coupled to said central tube.

21. The apparatus of claim 12, wherein said region, which has a plurality of micropores, forms a 360 degree band.

22. The apparatus of claim 21, wherein said region, which has a purality of micropores, is cylindrical.

* * * * *